United States Patent
Mukai et al.

(10) Patent No.: US 10,925,778 B2
(45) Date of Patent: Feb. 23, 2021

(54) ABSORBENT ARTICLE

(71) Applicant: UNICHARM CORPORATION, Shikokuchuo (JP)

(72) Inventors: Hirotomo Mukai, Kagawa (JP); Takahito Nagai, Kagawa (JP); Kuniyoshi Kawabata, Kagawa (JP); Naotaka Mimura, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 192 days.

(21) Appl. No.: 16/307,143

(22) PCT Filed: May 18, 2017

(86) PCT No.: PCT/JP2017/018629
§ 371 (c)(1),
(2) Date: Dec. 5, 2018

(87) PCT Pub. No.: WO2017/212886
PCT Pub. Date: Dec. 14, 2017

(65) Prior Publication Data
US 2019/0254884 A1    Aug. 22, 2019

(30) Foreign Application Priority Data

Jun. 6, 2016    (JP) .............................. JP2016-112631

(51) Int. Cl.
*A61F 13/494*    (2006.01)
*A61F 13/49*    (2006.01)
*A61F 13/496*    (2006.01)

(52) U.S. Cl.
CPC ...... *A61F 13/49406* (2013.01); *A61F 13/494* (2013.01); *A61F 13/49011* (2013.01);
(Continued)

(58) Field of Classification Search
CPC .......... A61F 13/49017; A61F 13/49406; A61F 13/49446; A61F 13/49453;
(Continued)

(56) References Cited

U.S. PATENT DOCUMENTS 5,582,606 A * 12/1996 Bruemmer ............ A61F 13/511
604/385.28
6,045,545 A *  4/2000 Vandemoortele ... A61F 13/4942
604/385.23
(Continued)

FOREIGN PATENT DOCUMENTS

CN           1878522 A      12/2006
CN         101909568 A      12/2010
(Continued)

OTHER PUBLICATIONS

International Search Report in PCT Application No. PCT/JP2017/018629, dated Aug. 15, 2017, 3pp.
(Continued)

*Primary Examiner* — Susan S Su
(74) *Attorney, Agent, or Firm* — Hauptman Ham, LLP

(57) ABSTRACT

An absorbent article includes an absorbent main body; a stomach-side member at an end portion on one side of the absorbent main body; and a back-side member at an end portion on another side. The absorbent main body has a pair of leak-proof walls in respective side end portions. Each of the leak-proof walls has a skin-side portion that includes a plurality of elastic members and a non-skin-side portion. The pair of leak-proof walls each have a joining portion in which mutually opposing surfaces of the skin-side portion and the non-skin-side portion are joined, and a non-joining portion above the joining portion. The mutually opposing surfaces are not joined in the non-joining portion. The joining portions are inward, with respect to the width direction, of leading ends of the leak-proof walls. Each of
(Continued)

the joining portions is overlapped with the stomach-side member or the back-side member in an up-down direction.

13 Claims, 10 Drawing Sheets

(52) U.S. Cl.
CPC .... *A61F 13/49017* (2013.01); *A61F 13/4942* (2013.01); *A61F 13/49061* (2013.01); *A61F 13/49413* (2013.01); *A61F 13/496* (2013.01)

(58) Field of Classification Search
CPC ............ A61F 13/49413; A61F 13/4942; A61F 13/4948; A61F 13/49493
See application file for complete search history.

(56) References Cited

U.S. PATENT DOCUMENTS

| | | | | |
|---|---|---|---|---|
| 7,192,422 | B2 * | 3/2007 | Otsubo | A61F 13/49001 |
| | | | | 604/385.201 |
| 8,771,250 | B2 * | 7/2014 | Carbonari | A61F 13/4942 |
| | | | | 604/385.28 |
| 2004/0030317 | A1 * | 2/2004 | Torigoshi | A61F 13/49014 |
| | | | | 604/385.27 |
| 2004/0122410 | A1 | 6/2004 | Itoh et al. | |
| 2008/0312631 | A1 * | 12/2008 | Okuda | A61F 13/49413 |
| | | | | 604/385.23 |
| 2010/0100069 | A1 * | 4/2010 | Nakaoka | A61F 13/4753 |
| | | | | 604/385.101 |
| 2010/0305532 | A1 * | 12/2010 | Ashton | A61F 13/5323 |
| | | | | 604/365 |
| 2011/0319855 | A1 * | 12/2011 | Lash | A61F 13/4942 |
| | | | | 604/385.25 |
| 2012/0035573 | A1 * | 2/2012 | Kuwano | A61F 13/49413 |
| | | | | 604/385.16 |
| 2012/0289921 | A1 * | 11/2012 | Hashino | A61F 13/49011 |
| | | | | 604/385.3 |
| 2013/0304011 | A1 * | 11/2013 | Sasayama | A61F 13/49446 |
| | | | | 604/370 |
| 2013/0324957 | A1 * | 12/2013 | Gassner | A61F 13/49011 |
| | | | | 604/365 |
| 2014/0148776 | A1 * | 5/2014 | Gassner | A61F 13/49011 |
| | | | | 604/385.24 |
| 2014/0288521 | A1 * | 9/2014 | Wade | A61F 13/49017 |
| | | | | 604/385.16 |
| 2015/0202094 | A1 * | 7/2015 | Inoue | A61F 13/49011 |
| | | | | 604/385.16 |
| 2016/0270972 | A1 * | 9/2016 | Surushe | A61F 13/49017 |
| 2016/0278996 | A1 * | 9/2016 | Takahashi | A61F 13/4942 |
| 2017/0000661 | A1 * | 1/2017 | Chatterjee | A61F 13/49017 |
| 2017/0266062 | A1 * | 9/2017 | Raycheck | A61F 13/51478 |

FOREIGN PATENT DOCUMENTS

| | | |
|---|---|---|
| CN | 202497341 U | 10/2012 |
| CN | 103282000 A | 9/2013 |
| CN | 104039291 A | 9/2014 |
| CN | 104302262 A | 1/2015 |
| CN | 108697539 A | 10/2018 |
| DE | 9321560 U1 | 9/1999 |
| EP | 1232736 A1 | 8/2002 |
| JP | 2005-218876 A | 8/2005 |
| JP | 2007-509725 A | 4/2007 |
| JP | 2011-206217 A | 10/2011 |
| JP | 2012-176227 A | 9/2012 |
| WO | 2009/084643 A1 | 7/2009 |

OTHER PUBLICATIONS

Extended European Search Report in EP Application No. 17810067.3, dated Apr. 9, 2019, 6pp.
International Preliminary Report on Patentability in PCT Application No. PCT/JP2017/018629, dated Aug. 15, 2017, 9pp.
Office Action in TW Application No. 106114674, dated Oct. 23, 2020, 3pp.
Office Action in CN Application No. 201780034775.2, dated Nov. 2, 2020, 11pp.

* cited by examiner

US 10,925,778 B2

ABSORBENT ARTICLE

RELATED APPLICATIONS

The present application is a National Phase of PCT/JP2017/018629, filed May 18, 2017, and claims priority based on Japanese Patent Application No. 2016-112631, filed Jun. 6, 2016.

TECHNICAL FIELD

The present invention relates to an absorbent article.

BACKGROUND ART

Disposable diapers such as pull-on diapers have been used conventionally. Patent Document 1 discloses a disposable diaper 1 in which a leak-proof cuff (leak-proof wall) 40A is formed on the two width-direction sides of a main body (absorbent main body) that includes an absorbent core 12. The leakage of excrement is prevented by putting the leak-proof cuffs 40A of this disposable diaper 1 into a raised state.

CITATION LIST

Patent Document

[Patent Document 1] JP 2005-218876A

SUMMARY OF INVENTION

Technical Problem

However, with the disposable diaper 1 in Patent Document 1, when the absorbent core 12 absorbs excrement, the main body becomes heavier, and the main body sags downward. Accordingly, there is a risk that gaps will form between the leak-proof cuffs 40A and the wearer's body, and that excrement will leak to the outside through leg open portions 9.

The present invention was achieved in light of the above-described problems, and an object of the present invention is to reduce the risk of the leakage of excrement to the outside by suppressing the formation of a gap between the absorbent article and the wearer's body by facilitating maintaining a flat-shaped portion that comes into contact with the wearer's body and that is formed in a leading end portion of a leak-proof wall by joining together portions thereof.

Solution to Problem

A primary aspect of the invention to achieve the above objective is an absorbent article having an up-down direction and including: an absorbent main body that has a longitudinal direction, a width direction, and a thickness direction that intersect each other; a stomach-side member arranged at an end portion on one side of the absorbent main body; and a back-side member arranged at an end portion on another side of the absorbent main body, wherein the absorbent main body has a pair of leak-proof walls in respective side end portions, the pair of leak-proof walls each have a skin-side portion that includes a plurality of elastic members and a non-skin-side portion that is arranged on a non-skin side of the skin-side portion, the pair of leak-proof walls each have a joining portion in which at least portions of mutually opposing surfaces of the skin-side portion and the non-skin-side portion are joined, and a non-joining portion that is provided above the joining portion in the up-down direction, the mutually opposing surfaces not being joined in the non-joining portion, the joining portions are provided inward, with respect to the width direction, of leading ends of the leak-proof walls, and each of the joining portions is at least partially overlapped with the stomach-side member or the back-side member in the up-down direction.

Other features of the present invention will become apparent from the present description and the attached drawings.

Advantageous Effects of Invention

According to the present invention, even if the absorbent main body absorbs excrement and becomes heavier, it is possible to reduce the risk of the leakage of excrement to the outside by suppressing the formation of a gap between the absorbent article and the wearer's body by facilitating maintaining a flat-shaped portion that comes into contact with the wearer's body and that is formed in a leading end portion of a leak-proof wall by joining together portions thereof.

DESCRIPTION OF EMBODIMENTS

Figure 1:
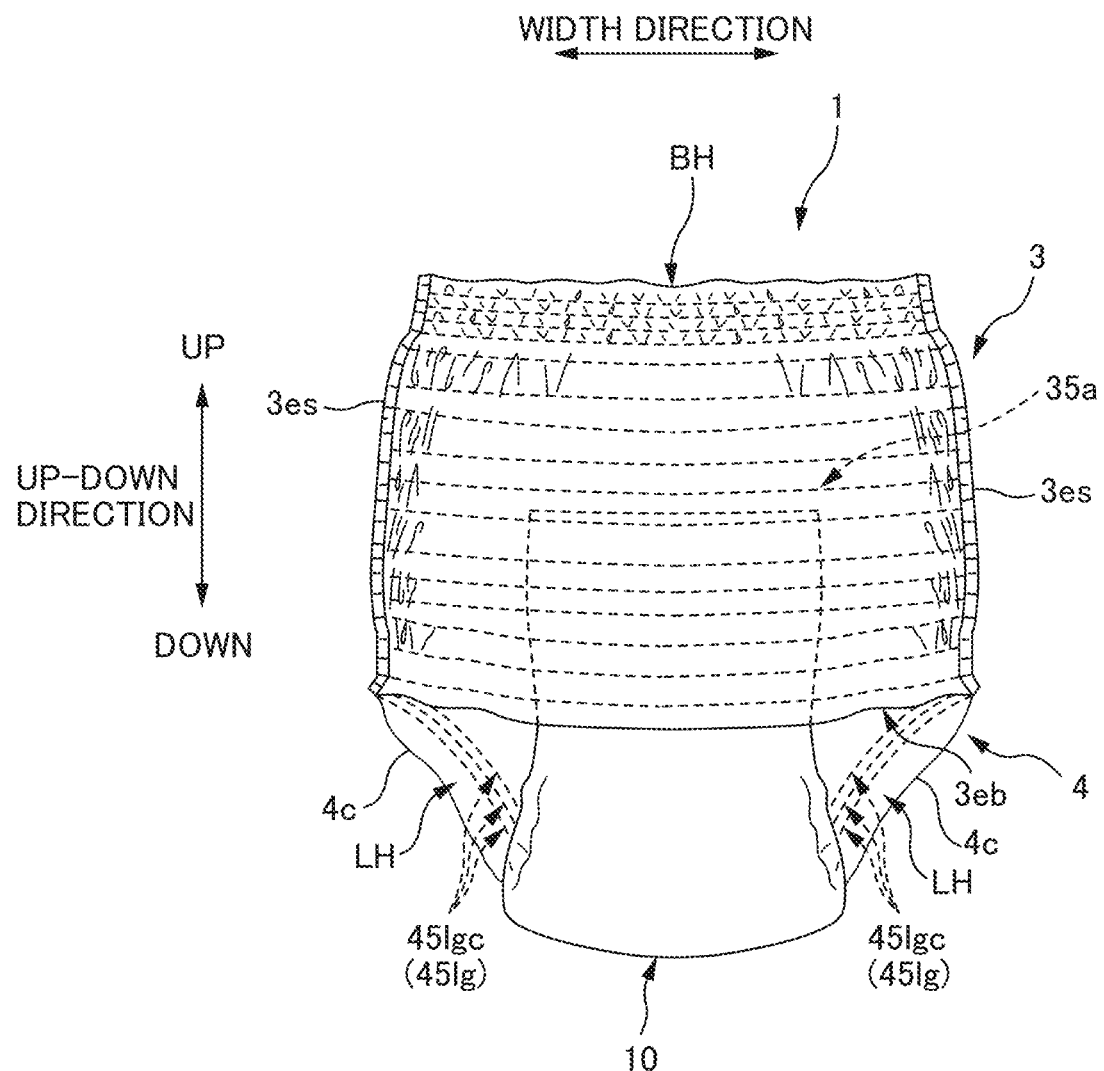
FIG. 1 is a schematic front view of a diaper 1 of a first embodiment as seen from the stomach side.

At least the following matters are made clear from the present description and the attached drawings.

Disclosed is an absorbent article having an up-down direction and including: an absorbent main body that has a longitudinal direction, a width direction, and a thickness direction that intersect each other; a stomach-side member arranged at an end portion on one side of the absorbent main body; and a back-side member arranged at an end portion on another side of the absorbent main body, wherein the absorbent main body has a pair of leak-proof walls in respective side end portions, the pair of leak-proof walls each have a skin-side portion that includes a plurality of elastic members and a non-skin-side portion that is arranged on a non-skin side of the skin-side portion, the pair of leak-proof walls each have a joining portion in which at least portions of mutually opposing surfaces of the skin-side portion and the non-skin-side portion are joined, and a non-joining portion that is provided above the joining portion in the up-down direction, the mutually opposing surfaces not being joined in the non-joining portion, the joining portions are provided inward, with respect to the width direction, of leading ends of the leak-proof walls, and each of the joining portions is at least partially overlapped with the stomach-side member or the back-side member in the up-down direction.

According to this absorbent article, the joining portion of each of the leak-proof walls is at least partially overlapped with the stomach-side member or the back-side member in the up-down direction of the absorbent article, and therefore even if the absorbent main body absorbs excrement and becomes heavier, it is possible to reduce the risk of the leakage of excrement to the outside by suppressing the formation of a gap between the absorbent article and the wearer's body by facilitating maintaining the flat-shaped portion that comes into contact with the wearer's body and that is formed in the leading end portion of the leak-proof wall by joining together portions thereof.

According to the absorbent article, wherein preferably each of the joining portions is at least partially overlapped with both the stomach-side member and the back-side member in the up-down direction.

According to this absorbent article, even if the absorbent main body becomes heavier, it is possible to reduce the risk of the leakage of excrement to the outside, by suppressing the formation of a gap between the absorbent article and the wearer's body by facilitating maintaining the flat-shaped portion of the leak-proof wall that comes into contact with the wearer's body.

According to the absorbent article, wherein preferably with respect to the up-down direction, the back-side member is longer than the stomach-side member, and for each of the joining portions, a region where the joining portion and the back-side member are overlapped is longer than a region where the joining portion and the stomach-side member are overlapped.

According to this absorbent article, when the length in the up-down direction of the back-side member, which needs to cover the buttocks portion, is set longer than the length in the up-down direction of the stomach-side member, the region where the joining portion and the stomach-side member are overlapped is set longer than the region where the joining portion and the back-side member are overlapped with respect to the up-down direction, and therefore even if the absorbent main body becomes heavier, it is possible to reduce the risk of the leakage of excrement to the outside, by suppressing the formation of a gap between the absorbent article and the wearer's body by facilitating maintaining the flat-shaped portion of the leak-proof wall that comes into contact with the wearer's body.

According to the absorbent article, wherein preferably a stomach-side adhesion region, in which the absorbent main body and the stomach-side member are adhered together, is provided in the end portion on the one side of the absorbent main body, a back-side adhesion region, in which the absorbent main body and the back-side member are adhered together, is provided in the end portion on the other side of the absorbent main body, and a lower end of the stomach-side member is located below the stomach-side adhesion region, or a lower end of the back-side member is located below the back-side adhesion region.

According to this absorbent article, the lower end portion of the stomach-side member or the lower end portion of the back-side member is not adhered to the absorbent main body, and therefore when the wearer puts on the absorbent article and then puts on clothes, there are cases where the lower end portion of the stomach-side member or the lower end portion of the back-side member comes into contact with the clothes and becomes folded back upward. Even if the absorbent article is worn along with clothes, and the weight of the absorbent main body increases due to absorbing excrement, due to the folded-back portion of the stomach-side member or the back-side member, it is possible to reduce the risk of the absorbent article falling downward, and to further maintain the flat-shaped portions of the leak-proof walls that come into contact with the wearer's body.

According to the absorbent article, wherein preferably the stomach-side elastic member is not arranged in a region extending from a lower end of the stomach-side adhesion region to the lower end of the stomach-side member in the up-down direction, or the back-side elastic member is not arranged in a region extending from a lower end of the back-side adhesion region to the lower end of the back-side member in the up-down direction.

According to this absorbent article, it is possible to reduce the risk that the folded-back lower end portion of the stomach-side member or the folded-back lower end portion of the back-side member contracts due to a stomach-side elastic member or a back-side elastic member, and due to the folded-back portions of the stomach-side member and the back-side member, it is possible to further reduce the risk of the absorbent article falling downward.

According to the absorbent article, wherein preferably the absorbent main body is provided on a skin side of the stomach-side member and the back-side member, a stomach-side adhesion region, in which the absorbent main body and the stomach-side member are adhered together, is provided in the end portion on the one side of the absorbent main body, a back-side adhesion region, in which the absorbent main body and the back-side member are adhered together, is provided in the end portion on the other side of the absorbent main body, and with respect to the width direction, the stomach-side adhesion region is located inward of two side ends of the absorbent main body, or the back-side adhesion region is arranged inward of the two side ends of the absorbent main body.

According to this absorbent article, the side end portions of the absorbent main body are not joined to the stomach-side member or the back-side member, and therefore it is possible to maintain a wide range of mobility for the wearer's legs at the leg openings in the absorbent article.

According to the absorbent article, wherein preferably at least a portion on the one side of each of the non-joining portions is provided in the stomach-side member and is located below a lowermost stomach-side elastic member among a plurality of stomach-side elastic members that extend in the width direction, or at least a portion on the other side of each of the non-joining portions is provided in the back-side member and is located below a lowermost back-side elastic member among a plurality of back-side elastic members that extend in the width direction.

According to this absorbent article, it possible to reduce the risk that the flat-shaped portion, which is formed in the leading end portion of each of the leak-proof walls by joining together portions of the leak-proof wall, contracts due to a stomach-side elastic member or a back-side elastic member, thus making it possible to further facilitate maintaining the state of contact with the wearer's body, so as to suppress the formation of a gap between the absorbent article and the wearer's body.

According to the absorbent article, wherein preferably the absorbent main body has a high rigidity region on at least either one of the one side and the other side, the high rigidity region having a higher rigidity than a lower portion of the absorbent main body, and an end portion on the at least one side of each of the joining portions is overlapped with at least a portion of the high rigidity region in the up-down direction.

According to this absorbent article, due to the high rigidity region of the absorbent main body and the end portion of each of the joining portions being overlapped with each other in the up-down direction, it is possible to suppress stretching/contraction caused by an elastic member of the stomach-side member or the back-side member, and it is possible to further facilitating maintaining the flat-shaped portion that comes into contact with the wearer's body and is formed in the leading end portion of each of the leak-proof walls by joining together portions of the leak-proof wall.

First Embodiment

Basic Configuration of Diaper 1

Figure 2:
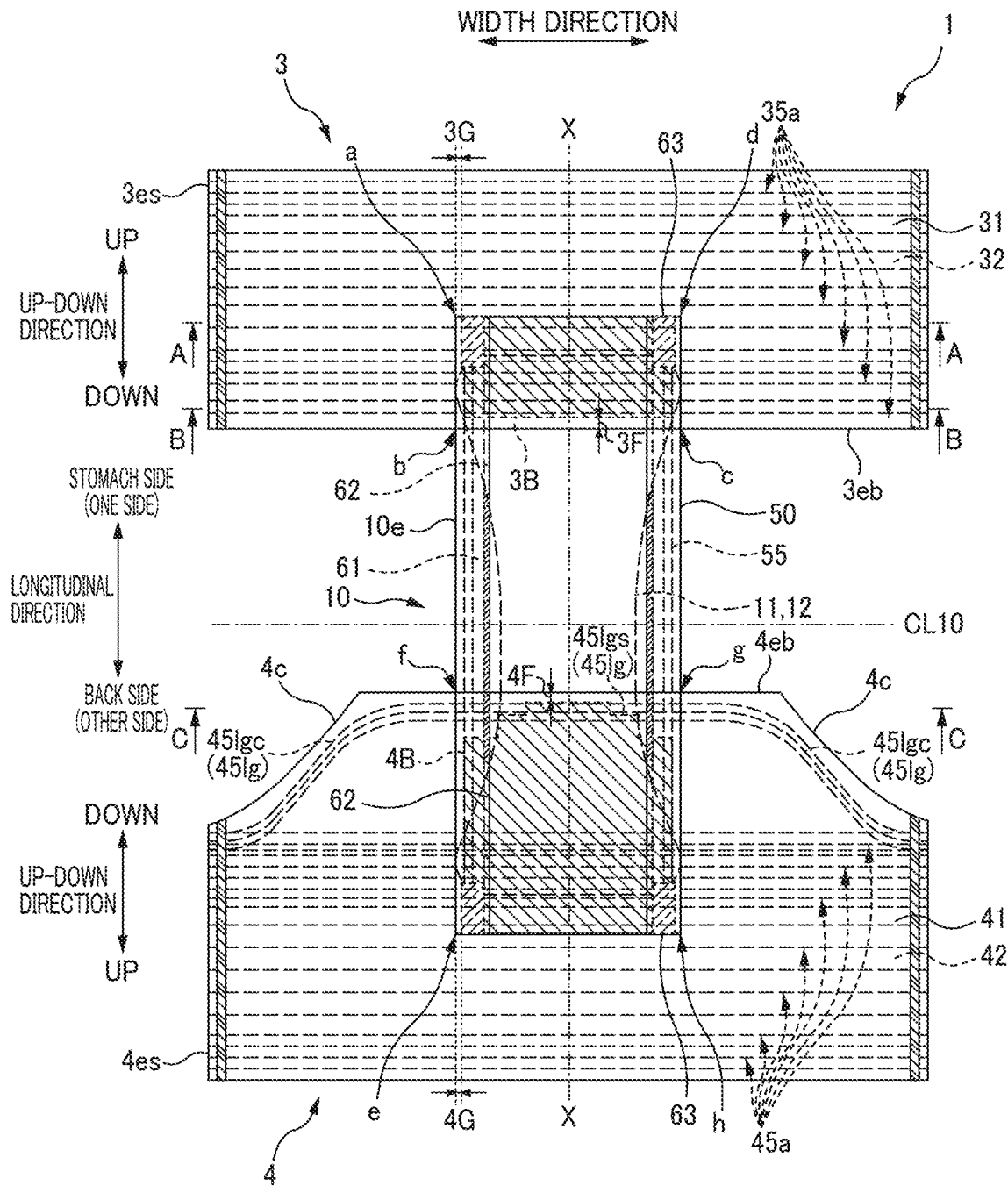
FIG. 2 is a plan view of the diaper 1 in an unfolded and stretched state.
Figure 3:
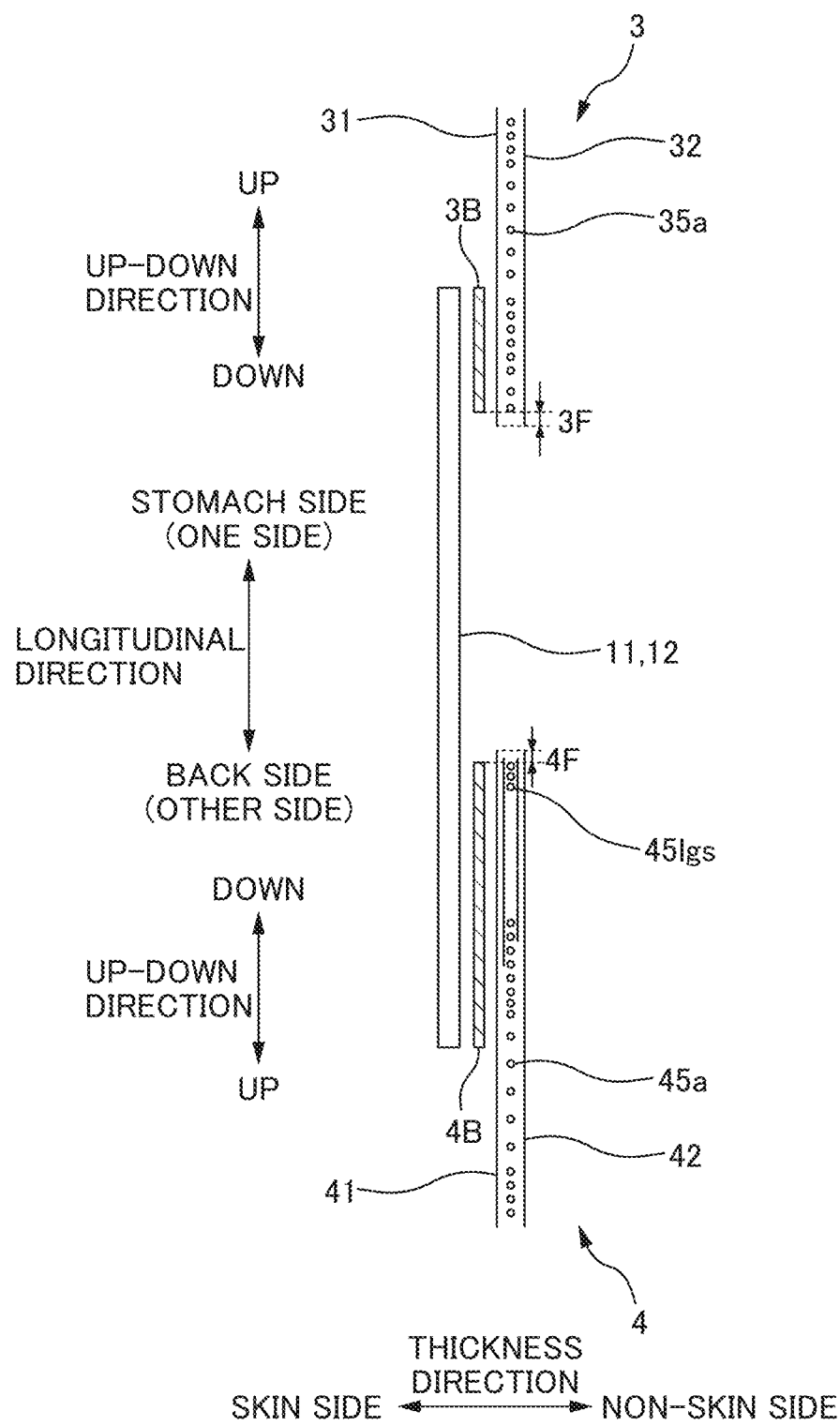
FIG. 3 is a cross-sectional view taken along X-X in FIG. 2.

The following describes the basic configuration of a pull-on disposable diaper 1 (hereinafter, also called the "diaper 1") as one example of an absorbent article according to the present embodiment. FIG. 1 is a schematic front view of the diaper 1 of a first embodiment as seen from the stomach side. FIG. 2 is a plan view of the diaper 1 in an unfolded and stretched state, and FIG. 3 is a cross-sectional view taken along X-X in FIG. 2. Note that the "stretched state" in FIG. 2 refers to the state where the product (diaper 1) is stretched such that no wrinkles are present, and specifically refers to a state in which the diaper 1 is stretched such that the dimensions of the constituent members thereof (e.g., a later-described back sheet 14) match or are close to the dimensions of the members on their own. Also, the scale in the thickness direction has been altered for the sake of convenience in FIG. 3.

In the pull-on state in FIG. 1, this diaper 1 has an up-down direction, a width direction, and a front-rear direction as three directions that are orthogonal to each other. In the following, the front side and the rear side in the front-rear direction in this pull-on state will be respectively referred to as the "stomach side" and the "back side".

Also, in the unfolded state in FIG. 2, the diaper 1 has a longitudinal direction and a width direction as three directions that are orthogonal to each other. In the following, "one side" and "another side" in the longitudinal direction in this unfolded state will also be respectively referred to as the "stomach side" and the "back side". Note that the width direction in the unfolded state is the same direction as the width direction in the pull-on state. Also, the longitudinal direction in the unfolded state is a direction that conforms to the up-down direction in the pull-on state. Moreover, as shown in FIGS. 3 and 4A to 4C, the direction orthogonal to the up-down direction (longitudinal direction) and the width direction will be called the "thickness direction", the side that comes into contact with the wearer's skin will be called the "skin side", and the side opposite thereto will be called the "non-skin side".

Also, the diaper 1 has a stomach-side member 3, a back-side member 4, and an absorbent main body 10 in the longitudinal direction. The stomach-side member 3 is a member that covers the stomach side of the wearer, the back-side member 4 is a member that covers the back side of the wearer, and the absorbent main body 10 is a member that is arranged at the wearer's crotch and absorbs excrement. In the unfolded state in FIG. 2, the stomach-side member 3 and the back-side member 4 are arranged parallel with each other with a gap therebetween, and the absorbent main body 10 spans the gap between the stomach-side member 3 and the back-side member 4.

When the diaper 1 is in the unfolded state in FIG. 2, the absorbent main body 10 is folded at a folding position at a predetermined position CL10 in the longitudinal direction (up-down direction) of the absorbent main body 10, and the stomach-side member 3 and the back-side member 4, which face each other in the folded state, are joined by welding or the like in side end portions 3es and side end portions 4es, and therefore the stomach-side member 3 and the back-side member 4 are connected together to form a ring shape, and a waist opening BH and a pair of leg openings LH are formed in the pull-on state of the diaper 1 as shown in FIG. 1.

At this time, the stomach-side member 3 is overlaid from the non-skin side onto the end portion on one side (stomach side) of the absorbent main body 10, specifically the rectangular region surrounded by points a, b, c, and d in FIG. 2, and the stomach-side member 3 is fixed thereto by adhesion in a stomach-side adhesion region 3B. The stomach-side adhesion region 3B is a region that is fixed by adhesion using an adhesive such as hot-melt that is applied thereto. At this time, with respect to the longitudinal direction, a lower end 3eb of the stomach-side member 3 is located on the other side of the stomach-side adhesion region 3B, and with respect to the width direction, the stomach-side adhesion region 3B is located inward of side ends 10e of the absorbent main body 10. In other words, in the pull-on state, with respect to the up-down direction, the lower end 3ed is located below the lower end of the stomach-side adhesion region 3B, and, inside the rectangular region surrounded by the points a, b, c, and d, the adhesive is not applied to a region 3F that is between the lower end of the stomach-side adhesion region 3B and the lower end 3eb of the stomach-side member 3, thus forming a region where the stomach-side member 3 and the absorbent main body 10 are not adhered to each other. Also, inside the rectangular region surrounded by the points a, b, c, and d, the adhesive is not applied to regions 3G that are between respective side ends of the stomach-side adhesion region 3B and the side ends 10e of the absorbent main body 10, thus forming regions where the stomach-side member 3 and the absorbent main body 10 are not adhered to each other.

Similarly, the back-side member 4 is overlaid from the non-skin side onto the end portion on the other side (back side) of the absorbent main body 10, specifically the rectangular region surrounded by points e, f, g, and h in FIG. 2, and the back-side member 4 is fixed thereto by adhesion in a back-side adhesion region 4B. The back-side adhesion region 4B is a region that is fixed by adhesion using an adhesive such as hot-melt that is applied thereto. At this time, with respect to the longitudinal direction, a lower end 4eb of the back-side member is located on the one side of the back-side adhesion region 4B, and with respect to the width direction, the back-side adhesion region 4B is located inward of the side ends 10e of the absorbent main body 10. In other words, in the pull-on state, with respect to the up-down direction, the lower end 4ed is located below the lower end of the back-side adhesion region 4B, and, inside the rectangular region surrounded by the points e, f, g, and h, the adhesive is not applied to a region 4F that is between the lower end of the back-side adhesion region 4B and the lower end 4eb of the back-side member 4, thus forming a region where the back-side member 4 and the absorbent main body 10 are not adhered to each other. Also, inside the rectangular region surrounded by the points e, f, g, and h, the adhesive is not applied to regions 4G that are between respective side ends of the back-side adhesion region 4B and the side ends 10e of the absorbent main body 10, thus forming regions where the back-side member 4 and the absorbent main body 10 are not adhered to each other.

Furthermore, inside the rectangular region surrounded by the points a, b, c, and d, elastic members 35a are not arranged in a region 3F that is between the lower end of the stomach-side adhesion region 3B and the lower end 3eb of the stomach-side member 3, and, inside the rectangular region surrounded by the points e, f, g, and h, elastic members 45a and 451g are not arranged in a region 4F that is between the lower end of the back-side adhesion region 4B and the lower end 4eb of the back-side member 4. In other words, the elastic members 35a are arranged above (on the one side of) the region 3F, and the elastic members 45a and 451g are arranged above (on the other side of) the region 4F.

The absorbent main body 10 has a function of absorbing excrement such as urine, has an approximately rectangular shape in a plan view as shown in FIG. 2, and is arranged at the center in the width direction, such that the longitudinal direction conforms to the up-down direction of the diaper 1. The absorbent main body 10 has a liquid-absorbent absorbent core 11 and a core-wrapping sheet 12 that covers the outer circumferential surface of the absorbent core 11. Also, leak-proof walls 50 are respectively provided on two sides in the width direction of the absorbent main body 10. The detailed configuration of the leak-proof walls 50 will be described later.

The absorbent core 11 includes liquid-absorbent fibers, such as pulp fibers, that are formed into a predetermined shape, with a superabsorbent polymer (so-called SAP) or the like being mixed with these fibers. In the present embodiment, the absorbent core 11 is approximately hourglass-shaped in a plan view. The core-wrapping sheet 12 is a liquid-permeable sheet member that covers the outer circumferential surface of the absorbent core 11, and can be constituted by tissue paper, nonwoven fabric, or the like.

The top sheet 13 is a liquid-permeable sheet member that is arranged on the skin-side surface in the thickness direction of the absorbent core 11 and comes into contact with the wearer's skin when the diaper is worn. The top sheet 13 is formed using, for example, an air-through nonwoven fabric, a spunbond nonwoven fabric, or the like.

The back sheet 14 is a liquid-impermeable sheet member that is arranged on the non-skin side in the thickness direction of the absorbent core 11, and constitutes a portion of the outer layer of the diaper 1. The back sheet 14 is formed using a resin film or the like, for example.

Also, the top sheet 13 and the back sheet 14 are joined to each other by adhesion, welding, or the like in portions that project in the longitudinal direction and the width direction from the absorbent core 11, and the absorbent core 11 is thus held between the top sheet 13 and the back sheet 14.

In the stomach-side member 3, a skin-side sheet 31 located on the wearer's skin side and a non-skin-side sheet 32 located on the side opposite to the wearer's skin are overlaid in the thickness direction. The skin-side sheet 31 and the non-skin-side sheet 32 have substantially the same shape, which is a substantially rectangular shape. They are also soft sheet members, and are formed by a nonwoven fabric or the like, for example.

Multiple stomach-side elastic members 35a, which are elastic strings or the like, are sandwiched and joined between the skin-side sheet 31 and the non-skin-side sheet 32 of the stomach-side member 3 in a state of being stretched in the width direction with a predetermined stretch factor. These stomach-side elastic members 35a give stretchability in the width direction to the stomach-side member 3 of the diaper 1.

In the back-side member 4, a skin-side sheet 41 located on the wearer's skin side, and a non-skin-side member 42 located on the side opposite to the wearer's skin are overlaid in the thickness direction. The skin-side sheet 41 and the non-skin-side sheet 42 have substantially the same shape, and each have a narrow portion 40c in which the central portion in the longitudinal direction (CL10 side) is constricted inward in the width direction. They are also soft sheet members, and are formed by a nonwoven fabric or the like, for example.

Multiple back-side elastic members 45a, which are elastic strings or the like, are sandwiched and joined between the skin-side sheet 41 and the non-skin-side sheet 42 of the back-side member 4 in a state of being stretched in the width direction with a predetermined stretch factor. These back-side elastic members 45a give stretchability in the width direction to the back-side member 4 of the diaper 1.

Also, in the back-side member 4, similarly to the back-side elastic members 45a, multiple back leg elastic members 451g are provided in the thickness direction between the skin-side sheet 41 and the non-skin-side sheet 42. The back leg elastic members 451g are arranged so as to extend from the longitudinally inward region of the back-side member 4 (the position toward the center in the longitudinal direction of the absorbent core 11) and curve along the narrow portions 4c. Specifically, the back leg elastic members 451g each include a linear portion 451gs that extends along the width direction in the central portion with respect to the width direction, and curved portions 451gc that curve laterally outward and diagonally upward from respective width-direction sides of the linear portion 451gs (FIG. 2).

Leak-Proof Wall 50

Figure 4A:
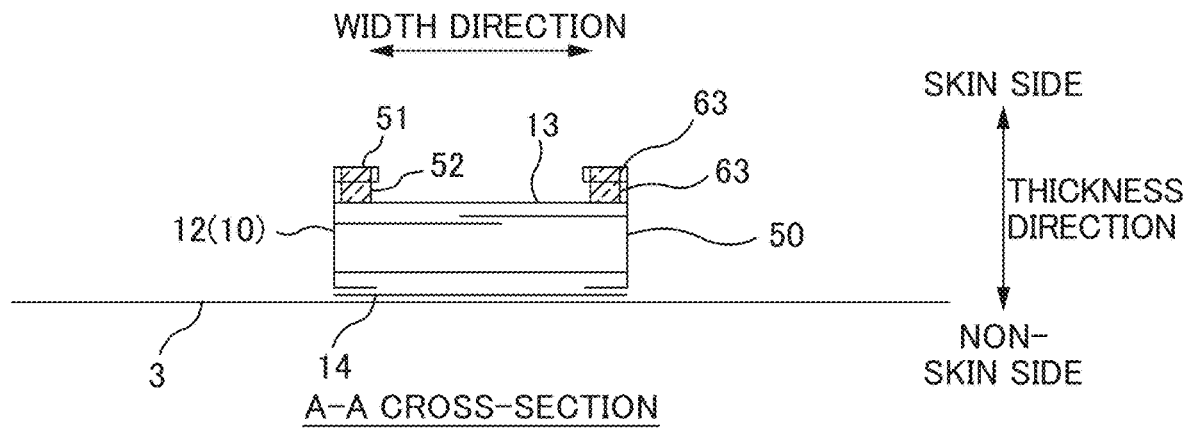
FIG. 4A is a cross-sectional view taken along A-A in FIG. 2.
Figure 4B:
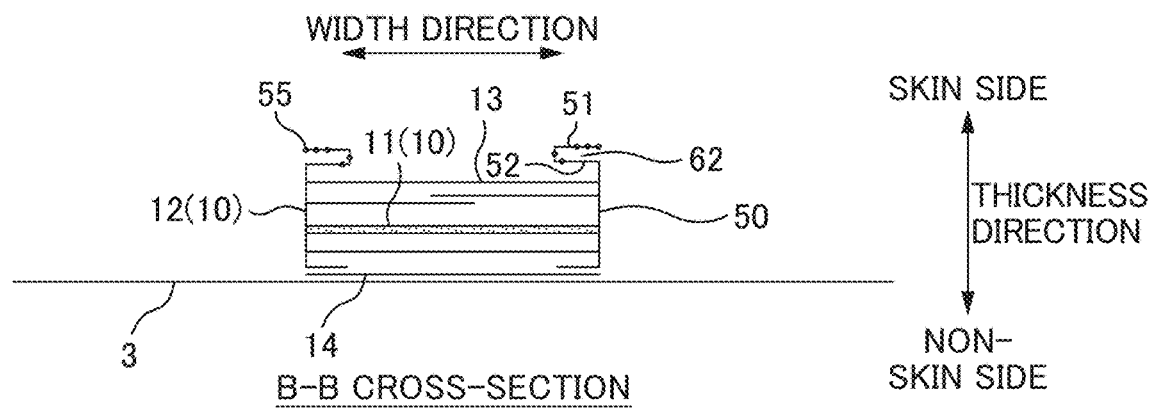
FIG. 4B is a cross-sectional view taken along B-B in FIG. 2.
Figure 4C:
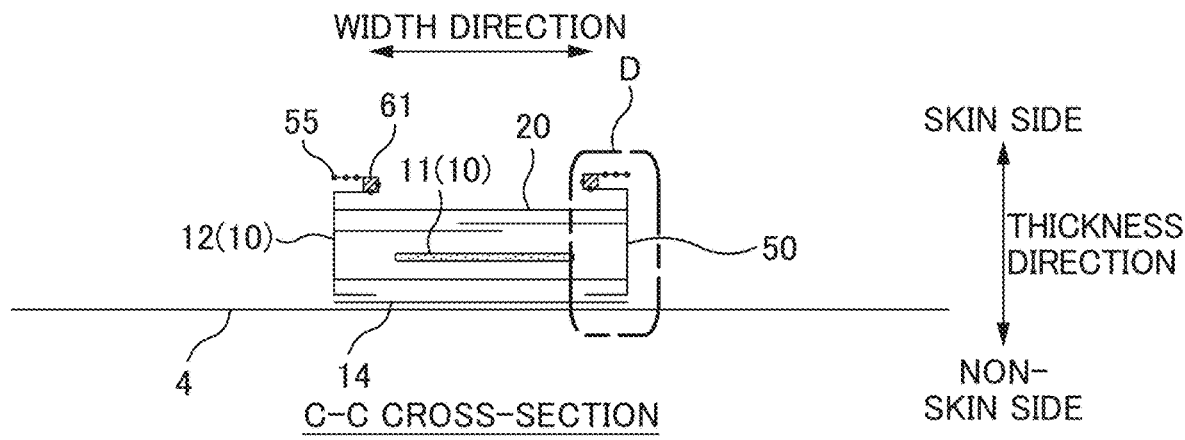
FIG. 4C is a cross-sectional view taken along C-C in FIG. 2.
Figure 5:
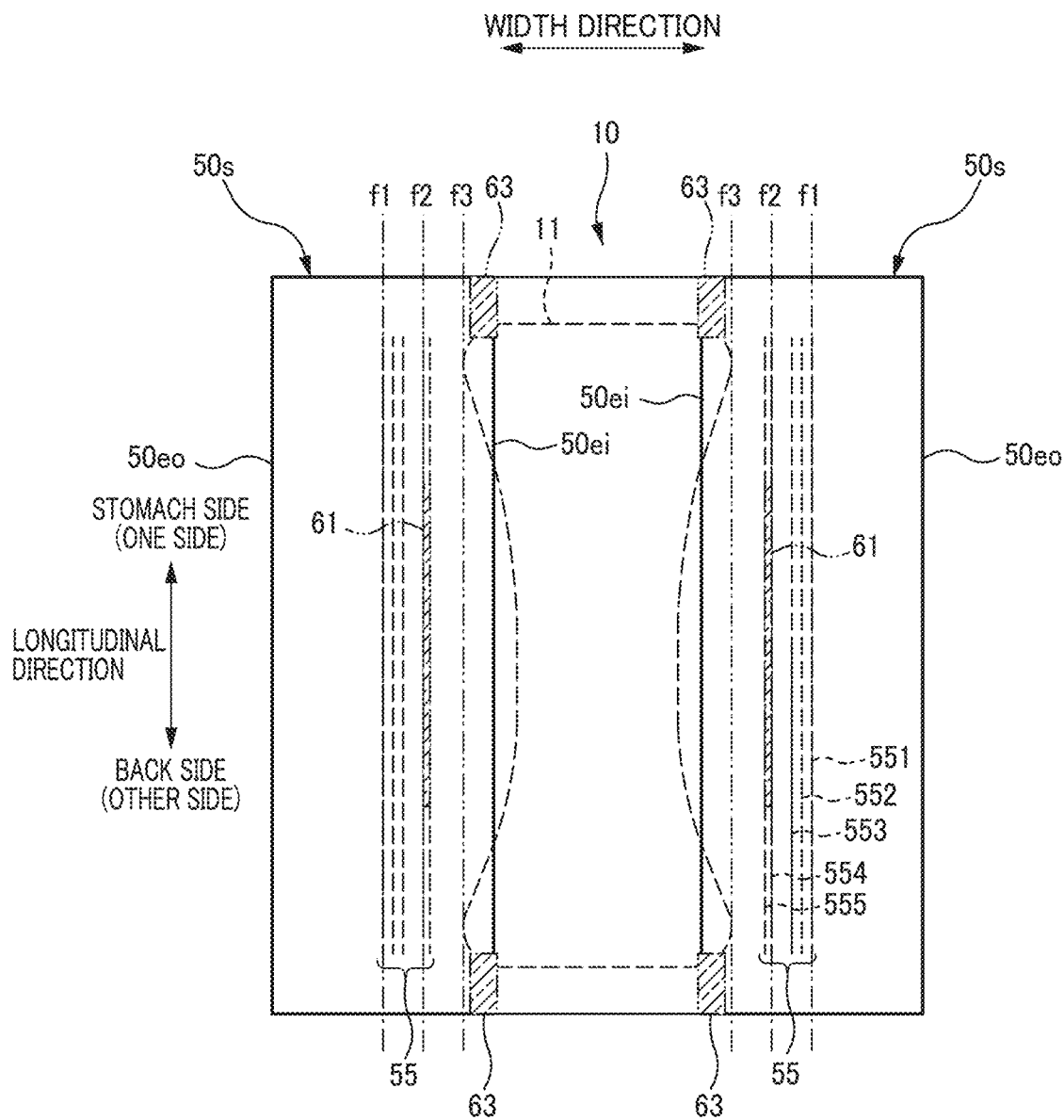
FIG. 5 is a plan view of an absorbent main body 10 in which leak-proof walls 50 are in an unfolded and stretched state.
Figure 6:
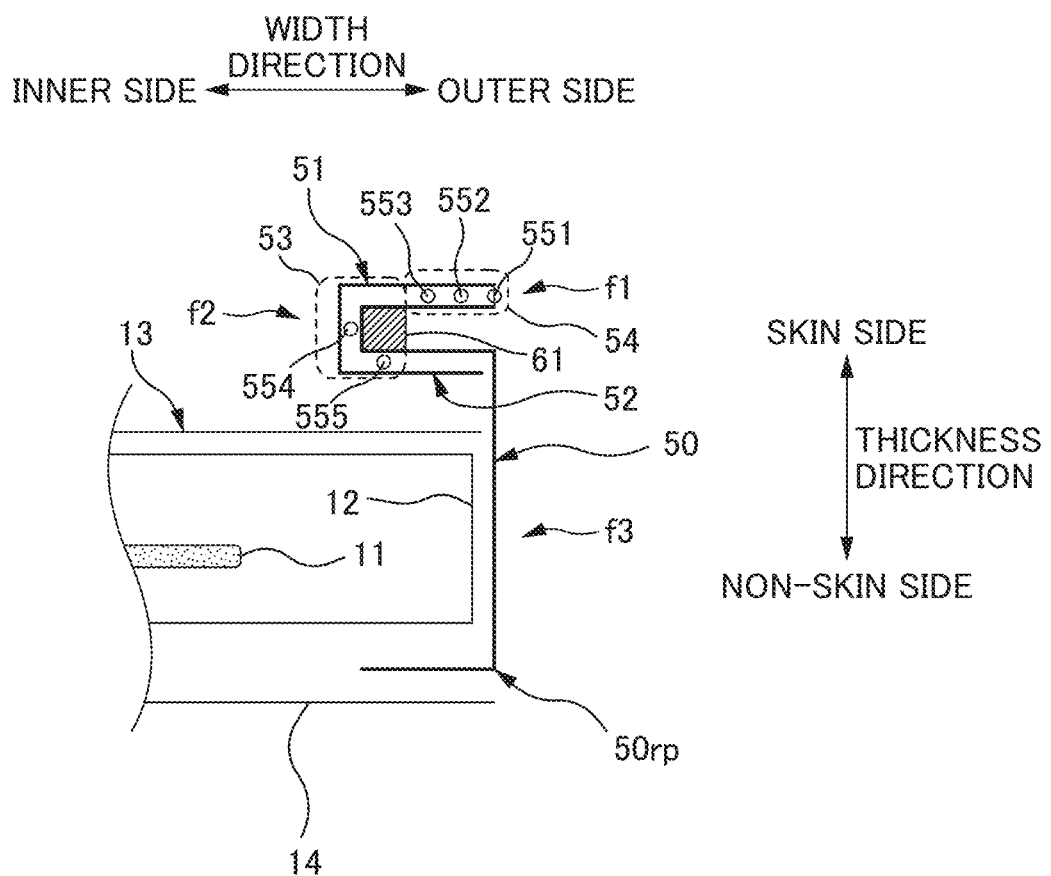
FIG. 6 is a diagram illustrating a region D in FIG. 4C.

Next, the leak-proof walls 50 will be described. The leak-proof wall 50 is arranged extending along the longitudinal direction of the absorbent main body 10 (the up-down direction of the diaper 1) on each of two width-direction sides of the absorbent main body 10, and the leak-proof walls 50 rise up from the side end portions of the absorbent main body 10 when the diaper 1 is worn, thus suppressing the leakage of excrement to the outside of the diaper 1. FIG. 4A is a cross-sectional view taken along A-A in FIG. 2, FIG. 4B is a cross-sectional view taken along B-B in FIG. 2, and FIG. 4C is a cross-sectional view taken along C-C in FIG. 2. FIG. 5 is a plan view of the absorbent main body 10 in which the leak-proof walls 50 are in an unfolded and stretched state. FIG. 6 is a diagram illustrating a region D in FIG. 4C. Note that the scale in the thickness direction is altered for the sake of convenience in FIGS. 4A to 4C and 6.

As shown in FIG. 5, the leak-proof walls 50 are each formed by folding the sheet member 50s in the width direction at folding lines f1 to f3 that extend in the longitudinal direction. The sheet member 50s that forms the leak-proof walls 50 can be constituted by a sheet member that has softness, such as a nonwoven fabric, for example. Also, multiple leak-proof wall elastic members 55, which are elastic strings or the like that have stretchability in the longitudinal direction, are joined to the leak-proof walls 50 in a state of being stretched with a predetermined stretch factor. In the present embodiment, leak-proof wall elastic members 551 to 555 are arranged side-by-side from outward to inward in the width direction. These leak-proof wall elastic members 55 give the leak-proof walls 50 stretchability in the longitudinal direction, and cause the leak-proof walls 50 to rise up when the diaper 1 is worn. The number of and arrangement of the leak-proof wall elastic members 55 is not limited to the configuration shown in FIG. 5, and appropriate modifications can be made according to the usage of the diaper 1.

In the unfolded state shown in FIG. 5, an inward end portion 50ei in the width direction of each leak-proof wall 50 (the sheet member 50s) is fixed by adhesion between the back sheet 14 and the absorbent core 11 covered by the core-wrapping sheet 12 in the thickness direction. Also, an outward end portion 50eo in the width direction of each leak-proof wall 50 (the sheet member 50s) protrudes outward in the width direction of the absorbent main body 10. In this state, the outward end portion 50eo is folded inward in the width direction with the folding line f1 serving as the base point, and portions of the sheet member 50s are joined to each other in the thickness direction with the leak-proof wall elastic members 551 to 555 sandwiched therebetween. At this time, among the leak-proof wall elastic members 55, the leak-proof wall elastic member 551 that is most outward in the width direction is matched with the position of the folding line f1 in the width direction.

Next, the sheet member 50s is folded inward in the width direction and to the non-skin side in the thickness direction, with the folding line f2 serving as the base point. The position of the folding line f2 in the width direction is substantially the same as the position of the leak-proof wall elastic member 554 in the width direction. Next, the sheet member 50s is folded inward in the width direction and to the skin side in the thickness direction, with the folding line f3 serving as the base point. Accordingly, as shown in FIGS. 4A to 4C and 6, this obtains the leak-proof wall 50 that is folded to be approximately S-shaped. Note that in the case of FIG. 6, the position of the folding line f3 serves as a base portion 50rp for when the leak-proof wall 50 is caused to rise up.

When the sheet member 50s is folded back from the one side to the other side in the width direction, a skin-side portion 51 of the leak-proof wall 50 is formed so as to be the farthest on the skin side in the thickness direction. The leak-proof wall elastic members 551 to 554 are provided between the folding line f1 and the folding line f2 in the skin-side portion 51. Also, a non-skin-side portion 52 is formed on the non-skin side of the skin-side portion 51 in the thickness direction. The leak-proof wall elastic members 554 and 555 are provided between the folding line f2 and the folding line f3 in the non-skin-side portion 52. Note that the leak-proof wall elastic member 554 is arranged at substantially the same position as the folding line f2 in the width direction, and therefore is deemed to be provided in both the skin-side portion 51 and the non-skin-side portion 52.

Also, the leak-proof wall 50 is provided with a pinch joining portion 61 obtained by joining mutually opposing surface portions of the skin-side portion 51 and the non-skin-side portion 52. Hereinafter, in the leak-proof wall 50, the region that includes the pinch joining portion 61 and is inward, with respect to the width direction, of the portion where the pinch joining portion 61 is formed will also be called a fold portion 53. In the present embodiment, the pinch joining portion 61, which is shown by diagonally downward hatching in FIG. 6, is provided in the region that is inward of the skin-side portion 51 (non-skin-side portion 52) in the width direction, and the fold portion 53 is also formed in this region. Note that the pinch joining portion 61 is formed by an adhesion means using an adhesive such as a hot-melt adhesive, or a crimping means such as embossing, for example. With respect to the width direction, the pinch joining portion 61 is provided inward of the leading end of the leak-proof wall 50 (toward the center in the width direction), and the skin-side portion 51 and the non-skin-side portion 52 are not joined to each other in the leading end portion of the leak-proof wall 50 (the outer side in the width direction) where the pinch joining portion 61 is not provided. Hereinafter, the region of the skin-side portion 51 where the skin-side portion 51 and the non-skin-side portion 52 are not joined will also be called a skin-side independent portion 54.

The pinch joining portion 61 is not provided in the region that is longitudinally outward of the pinch joining portion 61. Specifically, a non-joining portion 62, in which surfaces of the leak-proof wall 50 (sheet member 50s) that oppose each other in the thickness direction are not joined, is provided in the region of the leak-proof wall 50 on one side of the pinch joining portion 61 in the longitudinal direction and in the region on the other side. In this non-joining portion 62, the skin-side portion 51 and the non-skin-side portion 52 of the leak-proof wall 50 are not joined as shown in FIG. 4B, and therefore the fold portion 53 is not formed, and the entire region of the skin-side portion 51 in the width direction serves the skin-side independent portion 54.

Also, an end joining portion 63 is provided in each of two end portions in the longitudinal direction of the leak-proof wall 50. In each of the end joining portions 63, the skin-side portion 51 and the non-skin-side portion 52 of the leak-proof wall 50 are joined to each other, and the non-skin-side portion 52 and the top sheet 13 are joined to each other (FIG. 4A, etc.). Accordingly, in the end portions in the longitudinal direction of the leak-proof wall 50, the skin-side portion 51 and the non-skin-side portion 52 are fixed to the top sheet 13.

A portion of the pinch joining portion 61 is overlapped with the back-side member 4 in the up-down direction. In other words, as shown in FIG. 2, the end portion on the other side of the pinch joining portion 61 is located on the other side of (above) the lower end 4eb of the back-side member 4. At this time, the pinch joining portion 61 intersects the back leg elastic members 451g (linear portions 451gs), and is also overlapped with the back leg elastic members 451g in the up-down direction.

Figure 7A:
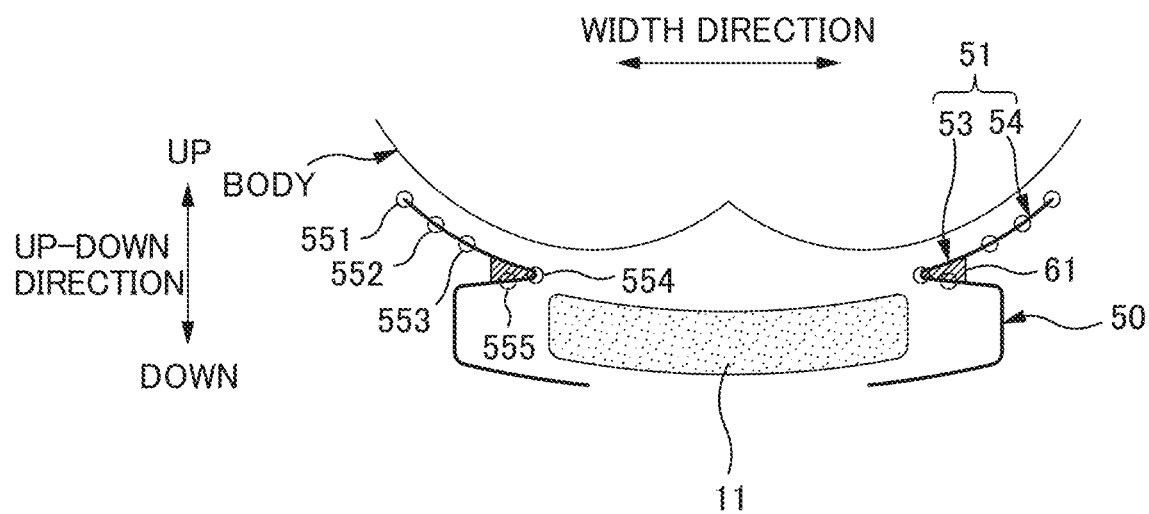
FIG. 7A is a diagram illustrating a worn state of the diaper 1 before excretion.
Figure 7B:
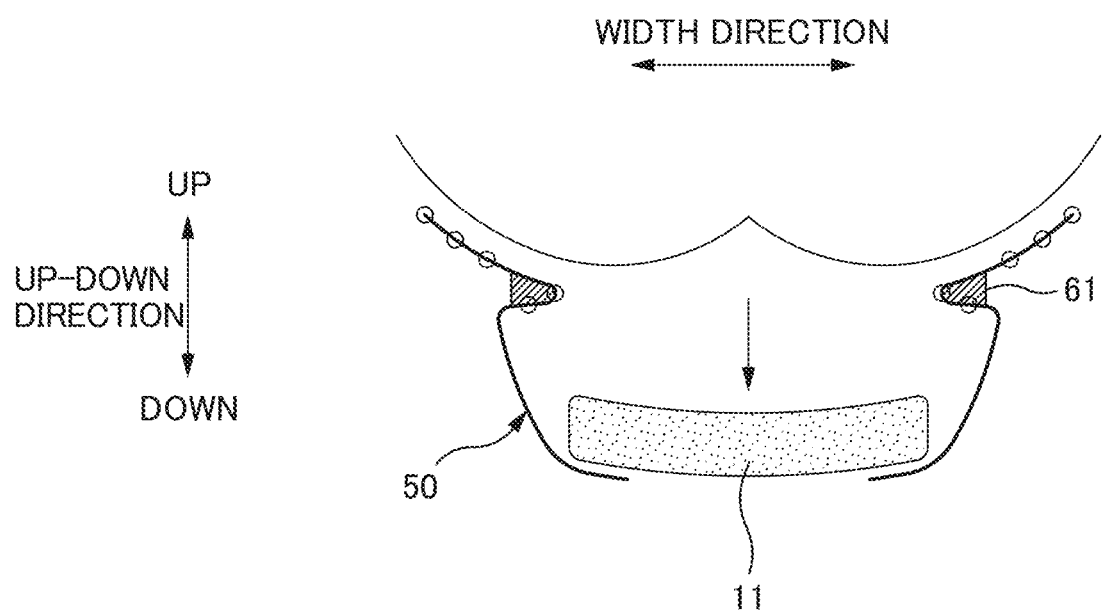
FIG. 7B is a diagram illustrating a worn state of the diaper 1 after excretion.

Using these dew-proof walls 50 makes it possible to suppress the formation of a gap in the crotch portion. FIG. 7A is a diagram illustrating a worn state of the diaper 1 before excretion. FIG. 7B is a diagram illustrating a worn state of the diaper 1 after excretion.

As shown in FIG. 7A, when the diaper 1 is worn, the skin-side portion 51, which is the portion of the leak-proof wall 50 that is arranged on the skin side, comes into contact with the wearer's body. Specifically, the skin-side portion 51 is arranged such that the entirety thereof comes into surface contact with the wearer's body. The pinch joining portion 61 has a higher rigidity due to the skin-side portion 51 and the non-skin-side portion 52 being overlapped and joined. For this reason, when contractive force is produced by the leak-proof wall elastic members 554 and 555, the skin-side portion 51 is firmly pressed against the wearer's body while maintaining a flat shape. Due to contraction of the leak-proof wall elastic member 555, the non-skin-side portion 52 and the skin-side portion 51 are simultaneously pressed up against the wearer's skin, and therefore the fold portion 53 is likely to come into contact (surface contact) with the wearer's skin while maintaining a flat shape. On the other hand, the skin-side independent portion 54 of the skin-side portion 51 has a lower rigidity than the fold portion 53, and therefore more easily deforms freely. For this reason, when the skin-side independent portion 54 is subjected to contractive force generated by the leak-proof wall elastic members 551 to 553 arranged therein, the skin-side independent portion 54 is pressed against the wearer's skin while forming a curved surface that conforms to protrusions and recessions in the shape of the wearer's body. Accordingly, the entirety of the skin-side portion 51 of the leak-proof wall 50 can be caused to fit closely and flatly against the wearer's body.

Effectiveness of Diaper 1 of Present Embodiment

Figure 8A:
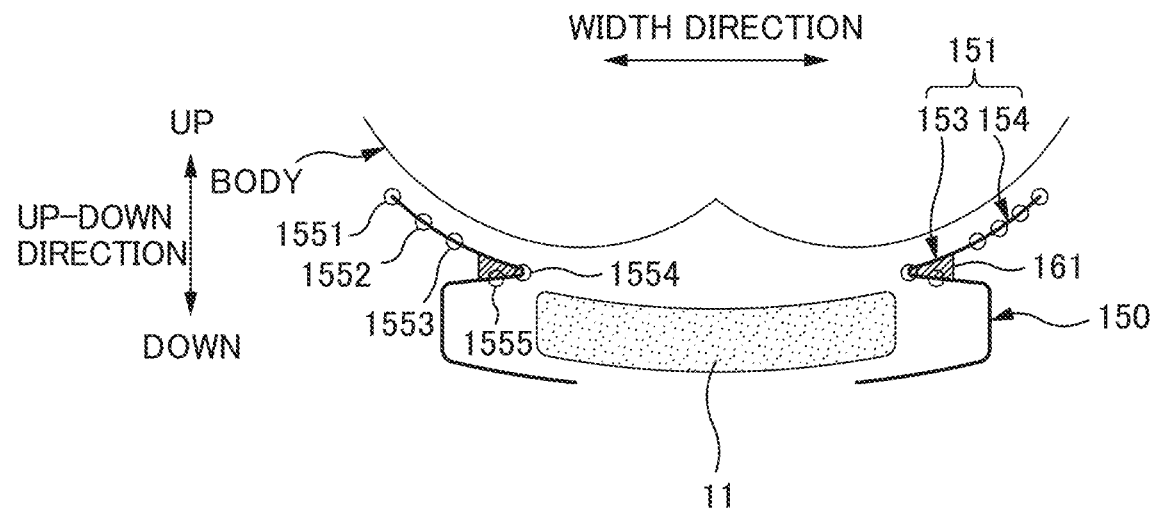
FIG. 8A is a diagram illustrating a worn state of a diaper 100 (comparative example) before excretion.
Figure 8B:
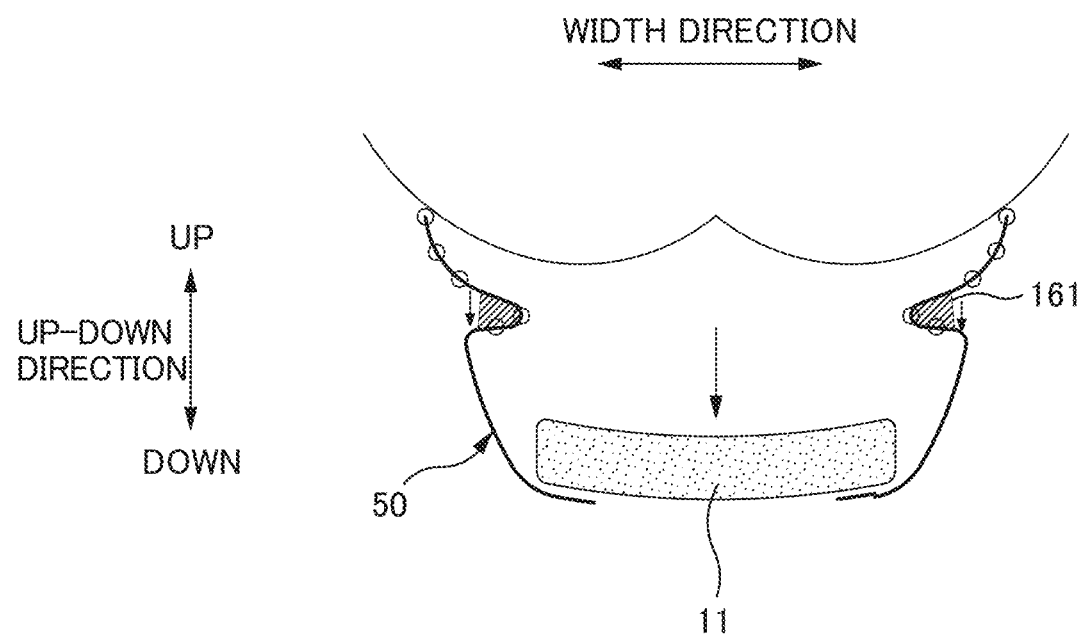
FIG. 8B is a diagram illustrating a worn state of the diaper 100 (comparative example) after excretion.

First, the following describes a problem that occurs when wearing a pull-on disposable diaper 100 (hereinafter, also called the "diaper 100") that has conventional leak-proof walls 150 as a comparative example. FIG. 8A is a diagram illustrating a worn state of the diaper 100 (comparative example) before excretion. FIG. 8B is a diagram illustrating a worn state of the diaper 100 (comparative example) after excretion.

The basic structure of the diaper 100 of this comparative example is substantially similar to that of the diaper 1 of the present embodiment, but is different in that a pinch joining portion 161 of the leak-proof wall of the diaper 100 is not overlapped with the stomach-side member 3 and the back-side member 4 in the up-down direction (longitudinal direction). A pair of leak-proof walls 150 are provided in two end portions in the width direction of an absorbent main body 110 (absorbent core 111), a plurality of elastic members 155 (elastic members 1551 to 1555 in FIG. 8A), which are elastic strings or the like, are provided in each of the leak-proof walls 150, and the leak-proof walls 150 rise upward due to contractive force generated by the elastic members 155. When the diaper 100 is worn, as shown in FIG. 8A, a skin-side portion 151 of each of the leak-proof walls 150 forms a flat shape due to the elastic members 1551 to 1555, and a skin-side independent portion 154 is pressed against the wearer's skin while forming a curved surface that corresponds to the wearer's body.

When excretion occurs in this state, the absorbent core 111 absorbs urine or the like and becomes heavier, and the leak-proof wall elastic members 155 are pulled downward and become stretched. Accordingly, a gap is formed between the wearer's skin and the skin-side portion 151 that had been in contact therewith as a flat surface. Specifically, as shown in FIG. 8B, in the skin-side portion 151, leak-proof walls 1552, 1553, and 1554 become stretched downward due to the weight of the absorbent core 111, and a gap is formed between the wearer's skin and the portion where the leak-proof walls 1552, 1553, and 1554 are provided. In this way, deformation occurs in the flat shape that had been in contact with the wearer's body before excretion, a gap is formed in the crotch portion, and there is a risk of excrement leaking to the outside.

On the other hand, the diaper 1 of the present embodiment has the pinch joining portion 61, in which opposing surfaces on the inward side in the width direction of the skin-side portion 51 and the non-skin-side portion 52 provided in the leak-proof wall 50 are joined together, and has the non-joining portion 62 above the pinch joining portion 61, and a portion of the pinch joining portion 61 is overlapped with the back-side member 4 in the up-down direction. In other words, as shown in FIG. 2, the end portion on the other side of the pinch joining portion 61 is overlapped with the back-side member 4. For this reason, in the portion where the pinch joining portion 61 and the back-side member 4 are overlapped, force acts in a direction according to which the back-side member 4 presses the skin-side portion 51 and the non-skin-side portion 52 of the leak-proof wall 50 to the skin side, and therefore the flat shape of the skin-side portion 51 is likely to be maintained. In other words, in the conventional diaper 100 (FIGS. 8A and 8B), the pinch joining portion 61 and the back-side member 4 (or the stomach-side member 3) are not overlapped, and therefore the flat shape of skin-side portion 151 of the leak-proof wall 150 in contact with the wearer's skin is maintained by only the leak-proof wall elastic members 155, but in the diaper 1 of the present embodiment, the flat shape of the skin-side portion 51 in contact with the skin is maintained by not only the elastic members 55, but also by the back-side member 4 (FIG. 7B). Due to contraction of the elastic members 45a and 451g of the back-side member 4, the absorbent main body 10, which includes the skin-side portion 51 and the non-skin-side portion 61, is further pressed against the skin. Specifically, due to the back-side member 4 that has the elastic members 45a and 451g, force acts in a direction according to which the non-skin-side portion 52, which is overlapped by the back-side member 4 from the non-skin side, presses the skin-side portion 51 to the skin side, and therefore the flat shape of the skin-side portion 51 in contact with the wearer's skin is likely to be maintained. As a result, a gap is not likely to be formed between the diaper 1 and the wearer's body, and it is possible to reduce the risk of the leakage of excrement to the outside.

Note that although a portion of the pinch joining portion 61 is overlapped with the back-side member 4 in the up-down direction in the diaper 1, there is no limitation to this. The pinch joining portion 61 and the stomach-side member 3 may be overlapped in the up-down direction. Even in the case where the pinch joining portion 61 and the stomach-side member 3 are overlapped, similarly to the back-side member 4, the flat-shaped portion of the leak-proof wall 50 (skin-side portion 51) is likely to be maintained, and it is possible to suppress the formation of a gap between the diaper 1 and the wearer's body.

Furthermore, it is further preferable that the end portion on the one side and the end portion on the other side of the pinch joining portion 61 are each overlapped with the stomach-side member 3 and the back-side member 4. Accordingly, the back-side member 3 or the stomach-side member 4 that is overlapped with the pinch joining portion 61 can further press the skin-side portion 51 and the non-skin-side portion 52 of the leak-proof wall 50 against the skin, and therefore the flat-shaped portion of the leak-proof wall 50 (skin-side portion 51) is more likely to be maintained.

In the case where the end portion on the one side and the end portion on the other side of the pinch joining portion 61 are each overlapped with the stomach-side member 3 and the back-side member 4, it is further preferable that, with respect to the up-down direction (longitudinal direction), the length of the region where the pinch joining portion 61 and the back-side member 4 are overlapped is longer than the length of the region where the pinch joining portion 61 and the stomach-side member 3 are overlapped. Normally, in a disposable diaper such as the diaper 1, the back-side member 4 that needs to cover the buttocks portion is longer in the up-down direction than the stomach-side member 3. For this reason, if the region where the pinch joining portion 61 and the back-side member 4 are overlapped is set longer in the up-down direction than the region where the pinch joining portion 61 and the stomach-side member 3 are overlapped, the flat-shaped portion of the leak-proof wall 50 (skin-side portion 51) is more likely to be maintained, and it is possible to further suppress the formation of a gap between the diaper 1 and the wearer's body.

Furthermore, in the diaper 1 of the present embodiment, the absorbent main body 10 is provided on the skin side of the stomach-side member 3 and the back-side member 4; the stomach-side adhesion region 3B, in which the absorbent main body 10 and the stomach-side member 3 are adhered together, is provided in the end portion on the one side (the region surrounded by the points a, b, c, and d) of the absorbent main body 10; and the back-side adhesion region 4B, in which the absorbent main body 10 and the back-side member 4 are adhered together, is provided in the end portion on the other side (the region surrounded by the points e, f, g, and h) of the absorbent main body 10. Also, the lower end 3eb of the stomach-side member 3 is located below the stomach-side adhesion region 3B, and the lower end 4eb of the back-side member 4 is located below the back-side adhesion region 4B. Specifically, as shown in FIGS. 3A and 3B, in the region surrounded by the points a, b, c, and d, the adhesive is not applied to the region 3F that is between the lower end 3eb of the stomach-side member 3 and the stomach-side adhesion region 3B, and stomach-side member 3 and the absorbent main body 10 are not adhered together in this region; and in the region surrounded by the points e, f, g, and h, the adhesive is not applied to the region 4F that is between the lower end 4eb of the back-side member 4 and the back-side adhesion region 4B, and the back-side member 4 and the absorbent main body 10 are not adhered together in this region.

Figure 9A:
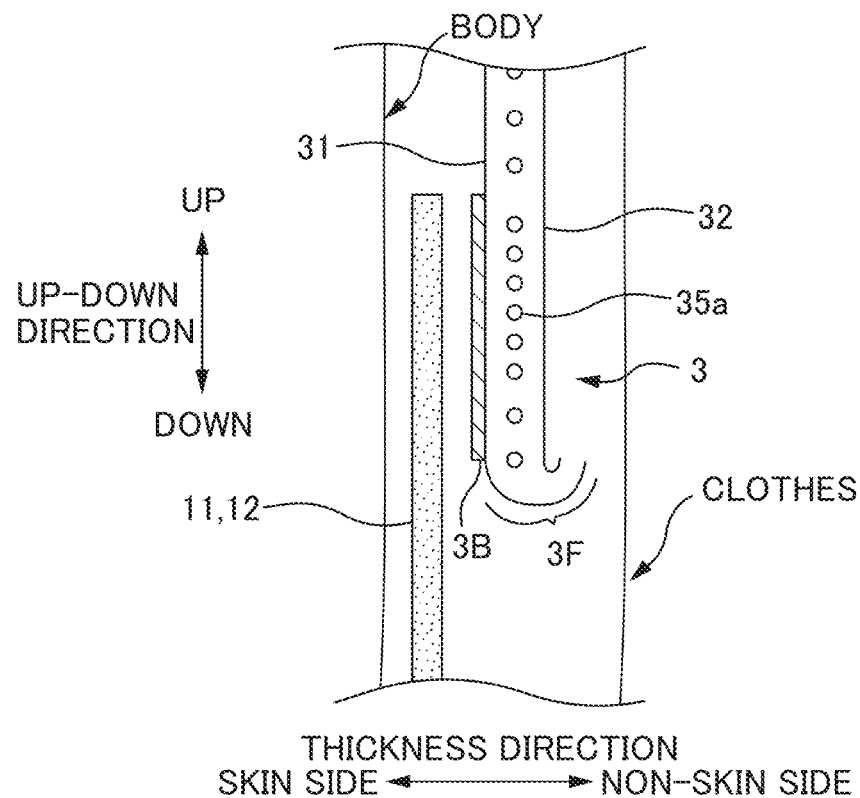
FIG. 9A is a diagram illustrating a portion of a stomach-side central cross-section taken in the width direction of the diaper 1 in a worn state.
Figure 9B:
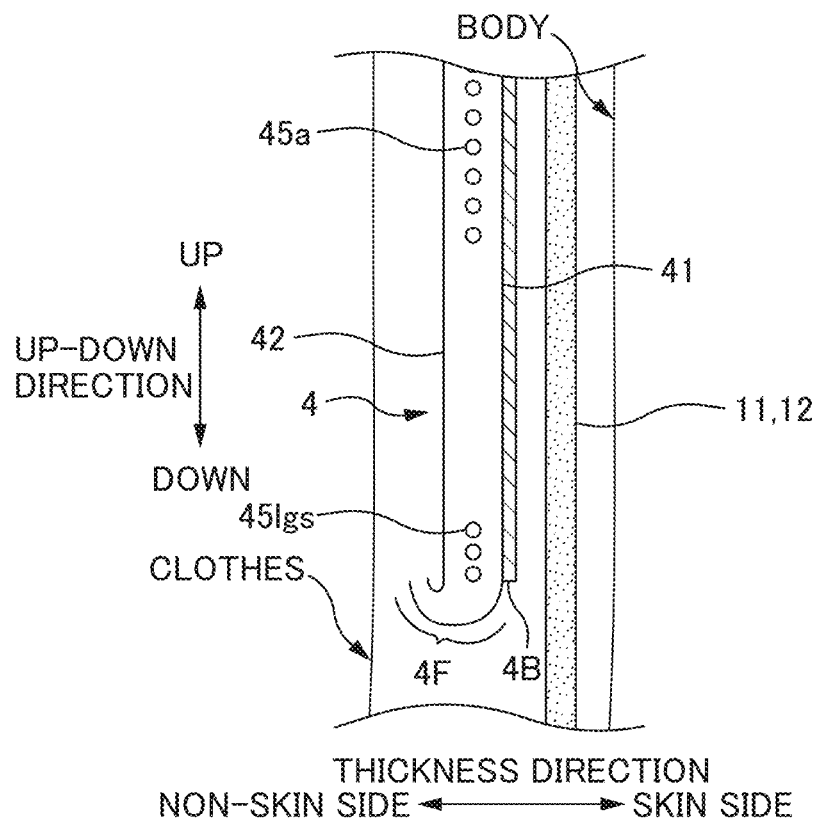
FIG. 9B is a diagram illustrating a portion of a back-side central cross-section taken in the width direction of the diaper 1 in a worn state.

FIG. 9A is a diagram illustrating a portion of a stomach-side central cross-section taken in the width direction of the diaper 1 in a worn state. FIG. 9B is a diagram illustrating a portion of a back-side central cross-section taken in the width direction of the diaper 1 in a worn state. As shown in FIG. 9A, when the wearer puts on the diaper 1 and then puts on clothes, there are cases where the region 3F portion of the stomach-side member 3, which is in contact with the clothes, becomes folded back upward. As shown in FIG. 9B, there are cases where the region 4F portion of the back-side member 4, which is in contact with the clothes, becomes folded back upward. In this way, if the region 3F (region 4F) not adhered to the absorbent main body 10 in the stomach-side member 3 (back-side member 4) becomes folded back upward and sandwiched between the wearer's stomach portion (back portion) and clothes, it is more likely for the folded-back portion (region 3F or 4F) to become caught on the clothes compared to the case where the region 3F (region 4F) portion is adhered to the absorbent main body 10 and the stomach-side member 3 (back-side member 4), and therefore even if the absorbent main body 10 becomes heavy, the diaper 1 is less likely to sag downward than in the case where the region 3F (region 4F) portion is adhered to the absorbent main body 10 and the stomach-side member 3 (back-side member 4), and it is possible to further suppress the risk of a gap forming between the wearer's body and the flat-shaped portion of the leak-proof wall 50.

Note that in the diaper 1 of the present embodiment, the lower end 3eb of the stomach-side member 3 is located below the stomach-side adhesion region 3B, and the lower end 4eb of the back-side member 4 is located below the back-side adhesion region 4B, but there is no limitation to this. This may apply to only either one of the two. It should be noted that with a configuration in which the lower end 3eb of the stomach-side member 3 is located below the stomach-side adhesion region 3B, and furthermore the lower end 4eb of the back-side member 4 is located below the back-side adhesion region 4B, it is possible to further suppress downward sagging of the diaper 1.

Furthermore, in the diaper 1 of the present embodiment, with respect to the up-down direction, the elastic members 35a are not arranged in the region 3F that extends from the lower end of the stomach-side adhesion region 3B to the lower end 3eb of the stomach-side member 3, and the elastic members 45a and 451g are not arranged in the region 4F that extends from the lower end of the back-side adhesion region 4B to the lower end 4eb of the back-side member 4. Accordingly, when the diaper is worn, it is possible to suppress the risk that the elastic members 35a, 45a, and 451g cause contraction in the width direction of the stomach-side member 3 in the region 3F and the back-side member 4 in the region 4F, which are folded back by the clothes, and therefore it is possible to further suppress the risk of downward sagging of the diaper 1.

Furthermore, in the diaper 1 of the present embodiment, with respect to the width direction, the stomach-side adhesion region 3B is located inward of the two side ends 10e of the absorbent main body 10, and the back-side adhesion region 4B is located inward of the two side ends 10e of the absorbent main body 10. Accordingly, it is possible to further reduce the width-direction size of the region where the absorbent main body 10 and the stomach-side member 3 (back-side member 4) are adhered together, and it is possible to further increase the range of mobility of the wearer's legs in the leg openings LH. Specifically, the greater the width-direction size of the adhesion region of the stomach-side member 3 (back-side member 4) and the absorbent main body 10 is, the more firmly the absorbent main body 10 can be supported by the stomach-side member 3 (back-side member 4), but the leg openings LH become smaller, and there is a risk of reducing the range in which the wearer can move their legs. For this reason, in the diaper 1, the stomach-side adhesion region 3B (back-side adhesion region 4B) is provided inward, in the width direction, of the two side ends 10e of the absorbent main body 10, thus making it possible to support the absorbent main body 10 that has become heavy due to absorbing excrement, while also increasing the size of the leg openings LH, and it is possible to further increase the range of mobility of the wearer's legs.

Note that in the present embodiment, with respect to the width direction, the stomach-side adhesion region 3B is located inward of the two side ends 10e of the absorbent main body 10, and the back-side adhesion region 4B is located inward of the two side ends 10e of the absorbent main body 10, but there is no limitation to this. A configuration is possible in which only the stomach-side adhesion region 3B is located inward of the two side ends 10e in the width direction, and a configuration is possible in which only the back-side adhesion region 4B is located inward of the two side ends 10e in the width direction. Note that with a configuration in which both the stomach-side adhesion region 3B and the back-side adhesion region 4B are located inward of the two side ends 10e of the absorbent main body 10, it is possible to further increase the range of mobility around the wearer's legs.

Second Embodiment

Basic Configuration of Diaper 2

Figure 10:
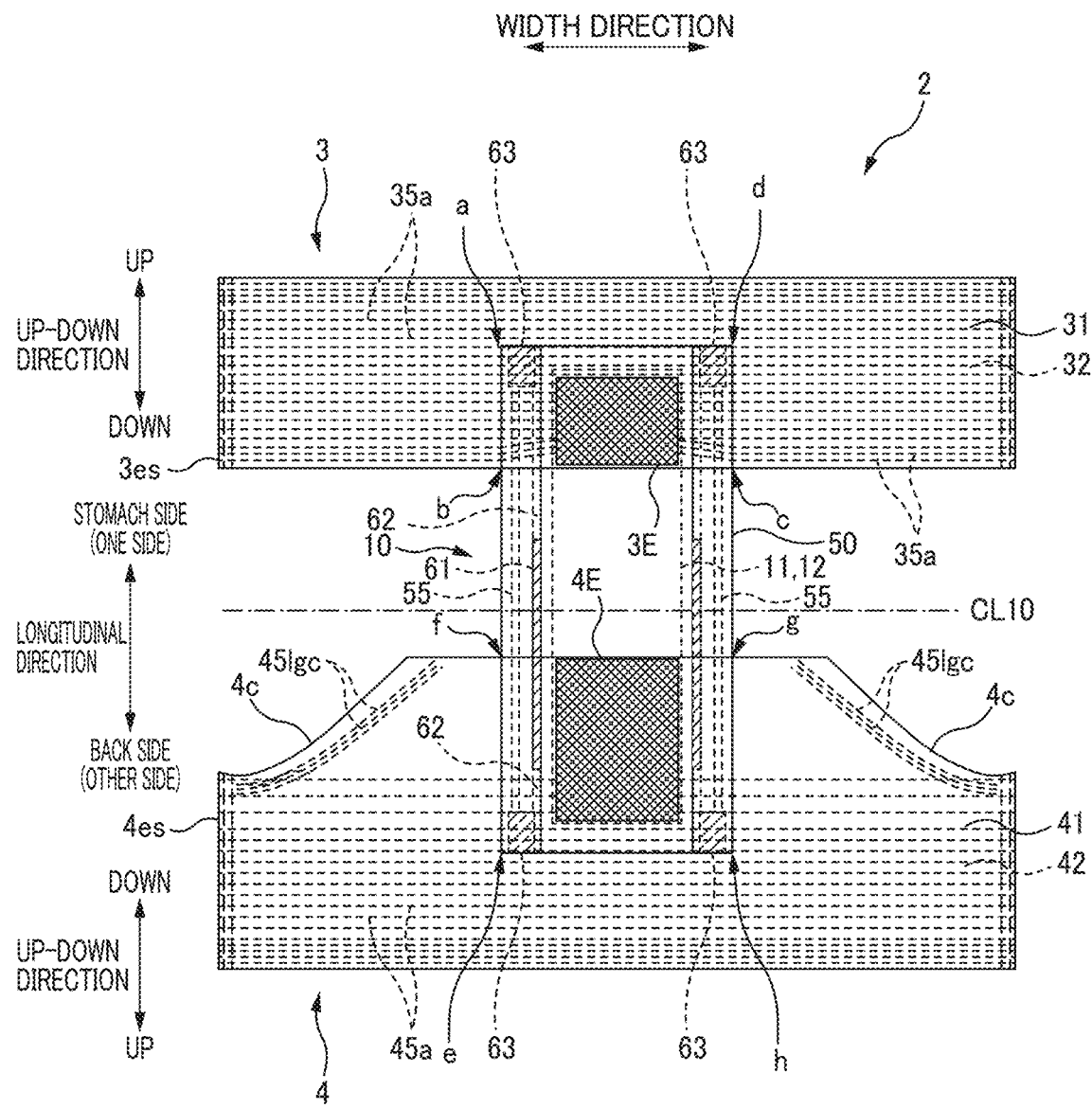
FIG. 10 is a plan view of a diaper 2 of a second embodiment in an unfolded and stretched state.

Next, the configuration of a diaper 2 according to a second embodiment of the present invention will be described with reference to FIG. 10. FIG. 10 is a plan view of the diaper 2 of the second embodiment in an unfolded and stretched state. In FIG. 10, configurations that are same as the described configurations of the diaper 1 of the first embodiment are denoted by the same reference signs, and descriptions will not be given for them.

Similarly to the diaper 1, the diaper 2 according to the present embodiment is a pull-on disposable diaper that has the stomach-side member 3, the back-side member 4, and the absorbent main body 10. An end portion (rectangular region surrounded by the points a, b, c, and d) on the one side (stomach side) of the absorbent main body 10 is overlapped by the stomach-side member 3 from the non-skin side and adhered and fixed thereto in a stomach-side adhesion region (not shown), and an end portion (rectangular region surrounded by the points e, f, g, and h) on the other side (back side) is overlapped by the back-side member 4 from the non-skin side and adhered and fixed thereto in a back-side adhesion region (not shown).

In the end portion on the one side of the absorbent main body 10 (the rectangular region surrounded by the points a, b, c, and d), the absorbent main body 10 is compressed in the thickness direction, thus forming a high rigidity region 3E that has a higher rigidity than the lower portion (the central portion in the longitudinal direction) of the absorbent main body 10. The high rigidity region 3E reduces the risk of the end portion on the one side of the absorbent main body 10 contracting inward in the width direction due to contraction of the elastic members 35a.

Similarly, in the end portion on the other side of the absorbent main body 10 (the rectangular region surrounded by the points e, f, g, and h), the absorbent main body 10 is compressed in the thickness direction, thus forming a high rigidity region 4E that has a higher rigidity than the lower portion (the central portion in the longitudinal direction) of the absorbent main body 10. The high rigidity region 4E reduces the risk of the end portion on the other side of the absorbent main body 10 contracting inward in the width direction due to contraction of the elastic members 45a.

When the diaper 2 is in the unfolded state in FIG. 10, the absorbent main body 10 is folded at a folding position at the predetermined position CL10 in the longitudinal direction (up-down direction) of the absorbent main body 10, and the stomach-side member 3 and the back-side member 4, which face each other, are joined by welding in the side end portions 3es and side end portions 4es, and therefore the waist opening BH (not shown) and the pair of leg openings LH (not shown) are formed in the pull-on state of the diaper 2.

The substantially rectangular skin-side sheet 31 and non-skin-side sheet 32 of the stomach-side member 3 are overlapped in the thickness direction, and the elastic members 35a, which are elastic strings or the like, are sandwiched and joined between the skin-side sheet 31 and the non-skin-side sheet 32.

The back-side member 4 has the skin-side sheet 41 and the non-skin-side sheet 42 that are overlapped in the thickness direction, have substantially the same shape, and each have a narrow portion 4c in which the central portion in the longitudinal direction (CL10 side) is constricted inward in the width direction. The elastic members 45a, which are elastic strings or the like, are sandwiched and joined between the skin-side sheet 41 and the non-skin-side sheet. Similarly to the elastic members 45a, multiple back leg elastic members 451gc are arranged between the skin-side sheet 41 and the non-skin-side sheet 42 so as to extend along the narrow portions 4c from inward regions, with respect to the longitudinal direction, of the back-side member 4 (positions toward the center in the longitudinal direction of the absorbent core 11), and diagonally upward and outward in the width direction. Note that in the diaper 2, the back leg elastic members 451g do not have linear portions 451gs that extend in the width direction of the diaper 1.

The absorbent main body 10 includes the absorbent core 11, the core-wrapping sheet 12, the top sheet 13, and the back sheet 14, and is provided with a pair of leak-proof walls 50. The absorbent core 11 of the diaper 2 is substantially rectangular in a plan view, and is formed by liquid-absorbent fibers, such as pulp fibers with SAP or the like mixed therein.

Similarly to the diaper 1, the leak-proof walls 50 are arranged extending along the longitudinal direction of the absorbent main body 10, and rise up from the side end portions of the absorbent main body when the diaper 2 is worn, so as to suppress the leakage of excrement to the outside of the diaper 2. The leak-proof walls 50 each have multiple leak-proof wall elastic members 55 in the longitudinal direction, and the leak-proof walls are raised upward when the diaper 2 is worn. Also, a skin-side portion (not shown) and a non-skin-side portion (not shown) are provided by folding back the sheet member (leak-proof wall 50), the pinch joining portion 61 is provided by joining mutually opposing surface portions of the skin-side portion and the non-skin-side portion, and the non-joining portion 62 is provided in which mutually opposing surfaces of the skin-side portion and the non-skin-side portion are not joined together.

In the diaper 2, the non-joining portions 62 are provided above (on the stomach side and on the back side) of the pinch joining portions 61 in the up-down direction, and portions of the pinch joining portions 61 are overlapped with the back-side member 4.

At this time, the portion of each of the non-joining portions 62 on the other side (back side) is located below (toward the center in the longitudinal direction) the elastic member 45a that is the lowest among the elastic members 45a that extend in the width direction of the back-side member 4. Specifically, as shown in FIG. 10, the pinch joining portion 61 is not overlapped with the elastic members 45a, and the back leg elastic members 451g do not have the linear portions 451gs as in the diaper 1, and therefore the pinch joining portion 61 is not overlapped with elastic members that extend in the width direction. For this reason, it is possible to reduce the risk of the portion of the pinch joining portion 61 on the back side contracting in the width direction due to elastic member, and it is possible to make it more likely to maintain the flat-shaped portion of the leak-proof wall 50 that comes into contact with the wearer's body.

Furthermore, in the diaper 2, back-side end portions of the pinch joining portions 61 are overlapped with a portion of the high rigidity region 4E in the up-down direction. Specifically, portions of the pinch joining portions 61 are provided on respective sides of a portion of the high rigidity region 4E. The high rigidity region 4E has a high rigidity due to being compressed, and therefore is a region that is less likely to undergo deformation than a region that is not compressed (the central portion in the longitudinal direction of the absorbent main body 10). For this reason, the portions of the pinch joining portions 61 that are overlapped, in the up-down direction, with a portion of the high-rigidity high rigidity region 4E are not likely to undergo deformation due to the high rigidity region 4E, and therefore it is possible to suppress deformation of flat-shaped portions of the skin-side portions 51 of the leak-proof walls 50 caused by contraction in the width direction due to the elastic members 45a and 451g, and it is possible to more easily maintain the flat shape for coming into contact with the wearer's body.

Note that although the high rigidity regions 3E and 4E are provided in both the stomach-side member 3 and the back-side member 4 in the diaper 2, it is possible to provide only the high rigidity region 3E, or only the high rigidity region 4E. Here, portions of the pinch joining portions 61 may be overlapped with the high rigidity region 3E and the high rigidity region 4E in the up-down direction, or portions of the pinch joining portions 61 may be overlapped with either one of the high rigidity regions. Note that by providing the high rigidity region in both the stomach-side member 3 and the back-side member 4, it is possible to further reduce the risk of deformation of the flat-shaped portions of the leak-proof walls 50, and if portions of the pinch joining portions 61 are overlapped with both of the high rigidity regions 3E and 4E, it is possible to even more easily maintain the flat-shaped portions of the leak-proof walls 50.

Other Embodiments

A description has been given of the embodiment of the present invention. The foregoing embodiment is for facilitating the understanding of the present invention and is not to be construed as limiting the present invention. The present invention may be modified and/or improved without departing from the gist thereof, and it goes without saying that the present invention encompasses any equivalents thereof. For example, the following modifications are possible.

Although examples of using elastic strings as the waist elastic members and the leak-proof wall elastic members are described in the above embodiments, these elastic members are not limited to being linear elastic members such as so-called elastic strings. For example, it is possible to use flat (belt-shaped) elastic members that have a predetermined width. Also, a configuration is possible in which the sheet members that constitute the leak-proof walls and the back sheet are sheet members that have stretchability (e.g., stretchable nonwoven fabric), thus eliminating the need to separately provide elastic members such as elastic strings.

LIST OF REFERENCE NUMERALS 1, 2 diaper (pull-on disposable diaper)
3 stomach-side member
3es side end portion
3eb lower end
31 skin-side sheet
32 non-skin-side sheet
3B stomach-side adhesion region
3E high rigidity region
3F region
4 back-side member
4es side end portion
4eb lower end
4c narrow portion
41 skin-side sheet
42 non-skin-side sheet
4B back-side adhesion region
4E high rigidity region
4F region
10 absorbent main body
10e side end
11 absorbent core
12 core-wrapping sheet
13 top sheet
14 back sheet
35a stomach-side elastic member
45b back-side elastic member
451g back leg elastic member
451gs linear portion
451gc curved portion
50 leak-proof wall
50s sheet member
50ei inward end portion
50eo outward end portion
50rp base portion
51 skin-side portion
52 non-skin-side portion
53 fold portion
54 skin-side independent portion
55 leak-proof wall elastic member
551-555 leak-proof wall elastic member
61 pinch joining portion (joining portion)
62 non-joining portion
63 end joining portion
100 diaper (comparative example)
110 absorbent main body
111 absorbent core
150 leak-proof wall
155 elastic member
1551-1555 elastic member
f1, f21, f3 folding line
BH waist opening
LH leg opening
CL10 central position

The invention claimed is:

1. An absorbent article, comprising:
an absorbent main body that has a longitudinal direction, a width direction, and a thickness direction that intersect each other;
a stomach-side member arranged at a first longitudinal end portion on a stomach side of the absorbent main body; and
a back-side member arranged at a second longitudinal end portion opposite to the first longitudinal end portion and on a back side of the absorbent main body,
wherein
the absorbent main body has side end portions in the width direction, and a pair of leak-proof walls respectively in the side end portions,
the pair of leak-proof walls each have
a skin-side portion that includes a plurality of elastic members, and
a non-skin-side portion that is arranged on a non-skin side of the skin-side portion,
the pair of leak-proof walls each have
a joining portion in which at least a portion of a first surface of the skin-side portion is joined to a portion of a second surface of the non-skin-side portion, the first surface opposing to the second surface in the thickness direction, and
a non-joining portion that is provided outward of the joining portion in the longitudinal direction, the first surface and the second surface being not joined in the non-joining portion, the joining portions are provided inward, in the width direction, of leading ends of the pair of leak-proof walls, and each of the joining portions is at least partially overlapped with the stomach-side member or the back-side member in the thickness direction.

2. The absorbent article according to claim 1, wherein each of the joining portions is at least partially overlapped with both the stomach-side member and the back-side member in the thickness direction.

3. The absorbent article according to claim 2, wherein the back-side member is longer than the stomach-side member in the longitudinal direction, and for each of the joining portions, a region where the joining portion and the back-side member are overlapped is longer, in the longitudinal direction, than a region where the joining portion and the stomach-side member are overlapped.

4. The absorbent article according to claim 3, wherein a stomach-side adhesion region, in which the absorbent main body and the stomach-side member are adhered together, is provided in the first longitudinal end portion on the stomach side of the absorbent main body, a back-side adhesion region, in which the absorbent main body and the back-side member are adhered together, is provided in the second longitudinal end portion on the back side of the absorbent main body, and an inner end of the back-side member is located inward of the back-side adhesion region in the longitudinal direction.

5. The absorbent article according to claim 4, wherein the back-side member includes a back-side elastic member, and the back-side elastic member is not arranged in a region extending from an inner end of the back-side adhesion region to the inner end of the back-side member in the longitudinal direction.

6. The absorbent article according to claim 1, wherein a stomach-side adhesion region, in which the absorbent main body and the stomach-side member are adhered together, is provided in the first longitudinal end portion on the stomach side of the absorbent main body, a back-side adhesion region, in which the absorbent main body and the back-side member are adhered together, is provided in the second longitudinal end portion on the back side of the absorbent main body, and an inner end of the stomach-side member is located inward of the stomach-side adhesion region in the longitudinal direction.

7. The absorbent article according to claim 6, wherein the stomach-side member includes a stomach-side elastic member, and the stomach-side elastic member is not arranged in a region extending from an inner end of the stomach-side adhesion region to the inner end of the stomach-side member in the longitudinal direction.

8. The absorbent article according to claim 1, wherein the absorbent main body is provided on a skin side of the stomach-side member and the back-side member, a stomach-side adhesion region, in which the absorbent main body and the stomach-side member are adhered together, is provided in the first longitudinal end portion on the stomach side of the absorbent main body, a back-side adhesion region, in which the absorbent main body and the back-side member are adhered together, is provided in the second longitudinal end portion on the back side of the absorbent main body, and the stomach-side adhesion region is located inward of the side end portions of the absorbent main body in the width direction.

9. The absorbent article according to claim 1, wherein the stomach-side member includes a plurality of stomach-side elastic members extending in the width direction, the plurality of stomach-side elastic members includes an innermost stomach-side elastic member in the longitudinal direction, and each of the non-joining portions includes at least a portion overlapping the stomach-side member in the thickness direction and located inward of the innermost stomach-side elastic member in the longitudinal direction.

10. The absorbent article according to claim 1, wherein the absorbent main body has a high rigidity region on at least one of the stomach side or the back side, the absorbent main body has an inner portion inward of the high rigidity region in the longitudinal direction, the high rigidity region having a higher rigidity than the inner portion of the absorbent main body, and each of the joining portions includes, on the at least one of the stomach side or the back side, an end portion overlapping at least a portion of the high rigidity region in the width direction.

11. The absorbent article according to claim 1, wherein the absorbent main body is provided on a skin side of the stomach-side member and the back-side member, a stomach-side adhesion region, in which the absorbent main body and the stomach-side member are adhered together, is provided in the first longitudinal end portion on the stomach side of the absorbent main body, a back-side adhesion region, in which the absorbent main body and the back-side member are adhered together, is provided in the second longitudinal end portion on the back side of the absorbent main body, and the back-side adhesion region is arranged inward of the side end portions of the absorbent main body in the width direction.

12. The absorbent article according to claim 1, wherein the back-side member includes a plurality of back-side elastic members extending in the width direction, the plurality of back-side elastic members includes an innermost back-side elastic member in the longitudinal direction, and each of the non-joining portions includes at least a portion overlapping the back-side member in the thickness direction and located inward of the innermost back-side elastic member in the longitudinal direction.

13. The absorbent article according to claim 1, wherein the pair of leak-proof walls each have a further non-joining portion where the first surface portion and the second surface are not joined, and in each of the pair of leak-proof walls, the joining portion is located between the non-joining portion and the further non-joining portion in the longitudinal direction.

* * * * *